United States Patent
Marten

(10) Patent No.: US 10,695,646 B2
(45) Date of Patent: Jun. 30, 2020

(54) SYSTEMS AND METHODS FOR GROUNDS MONITORING

(71) Applicant: Dish Network L.L.C., Englewood, CO (US)

(72) Inventor: Neil Marten, Lakewood, CO (US)

(73) Assignee: DISH Network L.L.C., Englewood, CO (US)

( * ) Notice: Subject to any disclaimer, the term of this patent is extended or adjusted under 35 U.S.C. 154(b) by 98 days.

(21) Appl. No.: 16/152,238

(22) Filed: Oct. 4, 2018

(65) Prior Publication Data

US 2020/0108303 A1 Apr. 9, 2020

(51) Int. Cl.
| | |
|---|---|
| *A63B 71/00* | (2006.01) |
| *A63B 71/06* | (2006.01) |
| *A63B 57/00* | (2015.01) |
| *G01N 33/24* | (2006.01) |
| *G05D 1/02* | (2020.01) |
| *G05D 1/00* | (2006.01) |

(52) U.S. Cl.
CPC .............. *A63B 71/06* (2013.01); *A63B 57/00* (2013.01); *G01N 33/246* (2013.01); *G05D 1/0088* (2013.01); *G05D 1/0287* (2013.01)

(58) Field of Classification Search
None
See application file for complete search history.

(56) References Cited

U.S. PATENT DOCUMENTS

| | | | |
|---|---|---|---|
| 6,241,622 B1* | 6/2001 | Gobush | A63B 24/0003 473/199 |
| 6,506,124 B1* | 1/2003 | Manwaring | A63B 57/00 473/198 |
| 7,117,660 B1* | 10/2006 | Colens | A01D 34/008 56/10.2 A |
| 9,382,003 B2* | 7/2016 | Burema | B64C 39/024 |
| 2005/0034437 A1* | 2/2005 | McMurtry | A01D 34/008 56/1 |
| 2005/0038578 A1* | 2/2005 | McMurtry | A01B 79/005 701/25 |
| 2008/0261711 A1* | 10/2008 | Tuxen | A63B 24/0021 473/199 |
| 2011/0166701 A1* | 7/2011 | Thacher | A01D 34/008 700/245 |
| 2011/0166715 A1* | 7/2011 | Hoffman | A01B 79/005 700/284 |

(Continued)

*Primary Examiner* — Paul A D'Agostino
(74) *Attorney, Agent, or Firm* — Seed IP Law Group LLP

(57) ABSTRACT

Systems and methods for grounds monitoring may include recreational grounds monitoring robots that move about a recreational ground measuring soil moisture at various selectable locations, performing security monitoring and/or identifying and tracking objects on the recreational ground, such as players, golf carts and golf balls. The recreational grounds monitoring robots may also monitor the recreational ground while at charging or docking stations along the boundaries or edges of the recreational ground. Data collected from such monitoring may be used to reduce water usage and enhance games played on the recreational ground by providing the player with the ability to easily locate, and thus track, the location and movement of the ball, while also to facilitating providing game statistics, leaderboard information, other game variations, interactive games and augmented games.

23 Claims, 6 Drawing Sheets

(56) References Cited

U.S. PATENT DOCUMENTS

| | | | | |
|---|---|---|---|---|
| 2011/0273723 A1* | 11/2011 | Haberer | .................... | F16P 3/14 |
| | | | | 356/614 |
| 2013/0153673 A1 | 6/2013 | Younis | ................. | A01G 25/165 |
| | | | | 239/1 |
| 2013/0210556 A1* | 8/2013 | Vilar | .................... | A63B 47/021 |
| | | | | 473/431 |
| 2014/0207282 A1* | 7/2014 | Angle | .................... | G05B 15/02 |
| | | | | 700/257 |
| 2015/0328503 A1* | 11/2015 | Vilar | .................... | A63B 47/021 |
| | | | | 473/460 |
| 2016/0157422 A1* | 6/2016 | Kohler | ................. | A01D 34/008 |
| | | | | 700/275 |
| 2016/0174459 A1* | 6/2016 | Balutis | ................... | B25J 9/1674 |
| | | | | 701/25 |
| 2016/0255763 A1* | 9/2016 | Canyon | ................. | A01B 79/005 |
| 2019/0299073 A1* | 10/2019 | Vollbrecht | ............... | A63B 1/00 |

* cited by examiner

SYSTEMS AND METHODS FOR GROUNDS MONITORING

TECHNICAL FIELD

The disclosure relates to monitoring systems and, particularly, to monitoring systems for outdoor recreational grounds.

BRIEF SUMMARY

Monitoring water usage and soil conditions at various locations on grass recreational grounds (such as on parks, golf courses, football fields, soccer fields, and other sports fields) is desirable for proper maintenance and health of the grass. However, combining systems for monitoring of water usage and soil conditions at any point on the recreational ground with tracking for balls or players for interactive games and for security purposes increases efficiency and reduces costs for performing such operations while increasing the ability to attract new customers, spectators, players and patrons. For example, games such as golf may be enhanced by providing the player with the ability to easily locate, and thus track, the location and movement of the ball. A current location of the player's ball may be displayed on the player's mobile device such that a player may be able to easily locate their ball on the golf course after each swing, in order to proceed with the game in a more efficient manner. Also, the player may be provided statistics regarding game play, such as driving distance, current score and distance from the ball to the hole on the golf course. Based on the ball's current location and path traveled, the player may be able to more efficiently compare and compete with other players, and improve skills and performance. Also, such statistics may be provided to facilitate other game variations, such as driving contests and "best ball" style tournaments, and other interactive and augmented games.

However, using GPS-enabled golf balls to perform ball or player location involves implementing costly technology and substantial interaction by the user with their mobile device, which distracts from the game. Such systems are also time-consuming, and take control away from the owner, manager or facilitator of the golf course, thus reducing opportunities for providing centrally managed game enhancements in a more efficient and less costly manner. In addition, sports facilities with large grass playing fields, such as golf courses, use large amounts of water to maintain the grass. Using recreational grounds monitoring robots with soil moisture sensing functionality enables more accurate regulation of water usage to reduce overall water consumption and environmental costs. Thus, described herein are systems and methods for grounds monitoring, which use recreational grounds monitoring robots distributed on the recreational ground to save costs by reducing water usage while also providing more efficient ball or player location.

BRIEF DESCRIPTION OF THE DRAWINGS

The components in the drawings are not necessarily to scale relative to each other. Like reference numerals designate corresponding parts throughout the several views.

DETAILED DESCRIPTION

Figure 1:
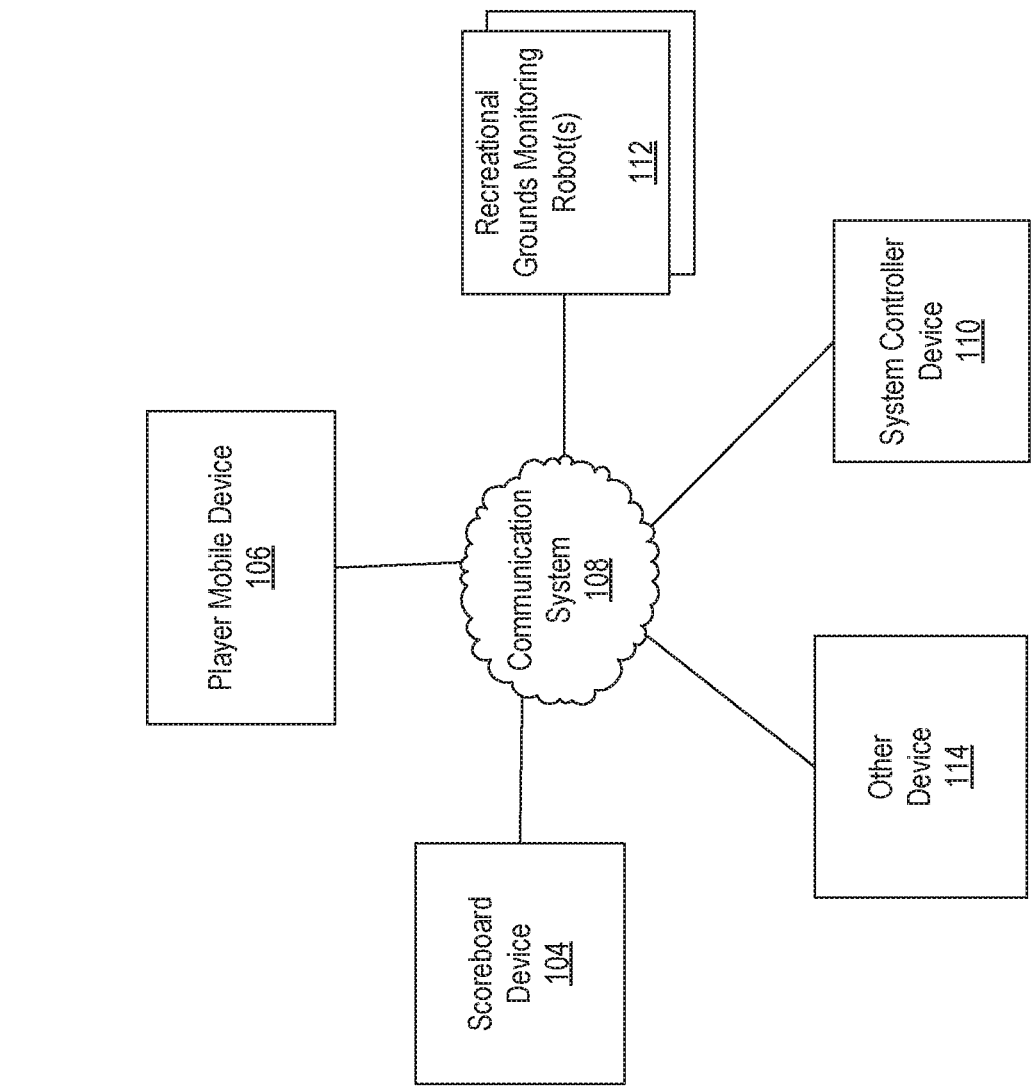
FIG. 1 is a block diagram illustrating an example environment in which embodiments of systems and methods for grounds monitoring may be implemented, according to one example embodiment.

FIG. 1 is a block diagram illustrating an example environment 102 in which embodiments of systems and methods for grounds monitoring may be implemented, according to one example embodiment.

Before providing additional details regarding the operation and constitution of systems and methods for grounds monitoring, the example environment 102, within which such systems and methods may operate, will be briefly described.

In the environment 102, a network of operable recreational grounds monitoring robots 112 is present on a grass recreational ground, such as a park, garden, golf course, soccer field, football field, field hockey field, etc. One or more of the recreational grounds monitoring robots 112 may be communicatively coupled directly or indirectly, such as via a communication system 108, to a system controller device 110, a player mobile device 106, a scoreboard device 104, and/or another device 114.

One or more of the recreational grounds monitoring robots 112 may interconnect to one or more communications media (such as a wireless computer network antenna, satellite antenna, telephone company switch, Ethernet portal, off-air antenna, or the like), data sources, or other devices (such as a system controller device 110, player mobile device 106, scoreboard device 104, other recreational grounds monitoring robots 112 or other device 114). The recreational grounds monitoring robots 112 measure the volumetric water content or water potential in soil, such as in the soil of golf courses, parks, grass sports fields and other recreational grounds. Overall, the term "grass sports field" and "grass recreational ground" as used herein includes any sports field or recreational ground with any amount of grass thereon, whether it covers the entire sports filed or recreational ground, or only one or more portions of the sports field or recreational ground.

Further, one or more of the recreational grounds monitoring robots 112 may include user interface devices, such as buttons or switches. In various embodiments, the recreational grounds monitoring robots 112 may be autonomous. For example, the recreational grounds monitoring robots 112 may operate and move autonomously throughout a recreational ground to perform some or all of the operations and processes described herein. The autonomous operation may be controlled by a robot motion control program 234 (shown in FIG. 2).

In some embodiments, the recreational grounds monitoring robots 112 may also or instead be controlled remotely by the system controller device 110 and/or player mobile device 106 to perform some or all of the operations and processes described herein. In many applications, a remote-control device (not shown) is operable to control the recreational grounds monitoring robots 112. The remote-control device typically communicates with the recreational grounds monitoring robot 112 using a suitable wireless medium, such as infrared ("IR"), radio frequency ("RF"), or the like. In some embodiments, the recreational grounds monitoring robots 112 may switch between an autonomous mode and a manual operation mode based on a signal or input provided by a user.

Each of the recreational grounds monitoring robots 112 distributed on the golf course has a ball or player detector that detects a ball or player being on the recreational ground or at a particular location on the recreational ground. For example, this detection may be accomplished via one or more sensors described above and/or other systems that may comprise the ball or player detector, including, but not limited to, one or more of: a video or still frame camera, an object recognition system, a laser scanning system (e.g., a light imaging, detection, and ranging (LiDAR) or scanning system), a motion sensor, a computer vision system, a video tracking system, a three-dimensional (3D) pose estimation system, a machine learning system, an indexing system, a motion estimation system, an image restoration system and a scene reconstruction system. In some embodiments, the ball or player detector of the recreational grounds monitoring robot 112 may detect an object detected on the recreational ground as being a ball or particular player or particular team member, and may also determine where on the recreational ground the detected object is located. For example, the recreational grounds monitoring robot 112 may determine its own location via triangulation, trilateration, time difference of arrival and/or time of arrival ranging systems based on two or more transmitters on the recreational ground at known locations providing locational or other beacon signals received by the recreational grounds monitoring robot 112. In some embodiments the recreational grounds monitoring robot 112 may also or instead use a global positioning system (GPS) of the recreational grounds monitoring robot 112 to determine its own location on the recreational ground.

Based on the current location of the recreational grounds monitoring robot 112 on the recreational ground when the object is detected, the direction the camera of the ball or player detector of the recreational grounds monitoring robot 112 is pointed when the object on the recreational ground is detected, and the size of the object in the video or image captured by the recreational grounds monitoring robot 112 (to aid in determining distance of the object from the recreational grounds monitoring robot 112), the location on the recreational ground of the detected object may be determined using one or more of the detection systems that may comprise the ball or player detector. For example, a computer vision system of the ball or player detector may be used to reconstruct a 3D model of the scene depicted in one or more images of the object captured by the recreational grounds monitoring robot 112. One or more other images of the detected object captured at the same time by one or more other recreational grounds monitoring robots 112 at different known locations on the recreational ground may also be used to aid in the computer vision and/or triangulation process used to determine the location of the detected object by providing further data points to more accurately pinpoint the location of the object. In this manner, the detected object need not have built-in GPS or other object location technology for the recreational grounds monitoring robot 112, player mobile device 106 or system controller device 110 to determine where on the recreational ground the detected object is located.

In some embodiments, detection of a ball on the recreational ground may be accomplished via one or more of a magnetometer, vibration detector and motion sensor of the recreational grounds monitoring robot 112. In the case of the recreational grounds monitoring robot 112 using a magnetometer, the ball will have a type of metal on the surface and/or interior of the ball that activates the magnetometer. The amount of metal in the ball is sufficient to activate the magnetometer when the ball is within a desired proximity to the recreational grounds monitoring robot 112. For example, the amount of metal on the surface and/or interior of the ball may be in an amount sufficient to activate the magnetometer when the ball is within 5 feet of the recreational grounds monitoring robot 112. Other distances, such as any falling within 1-40 feet or more, may also be selected, and the applicable amount of metal is then provided on and/or in the ball in a sufficient amount such that the magnetometer is activated when the ball is within the selected distance from the recreational grounds monitoring robot 112.

In response to detection of the ball or player being detected by the recreational grounds monitoring robot 112, the recreational grounds monitoring robot 112 may generate a first electronic signal indicative of the ball or player being detected by the recreational grounds monitoring robot 112. The recreational grounds monitoring robot 112 may then communicate the first electronic signal indicative of the ball or player being detected by the recreational grounds monitoring robot 112. For example, the recreational grounds monitoring robot 112 may then communicate, via communication system 108, the first electronic signal indicative of the ball or player being detected by the recreational grounds monitoring robot 112 to the system controller device 110, player mobile device 106, scoreboard device 104 and/or another device 114. In one embodiment, the system controller device 110 may process this signal and/or combine such information with other data received from one or more recreational grounds monitoring robots 112, player account information, game rules, player preference information, etc., to provide information to one or more players regarding a game score and/or other game play statistics based on the ball or player being detected by a particular recreational grounds monitoring robot 112.

For example, the system controller device 110 may have information regarding the locations of all the recreational grounds monitoring robots 112. These locations may be represented based on relative location to each other of the recreational grounds monitoring robots 112, and/or specific location coordinates of the recreational grounds monitoring robot in a two-dimensional (2D) or three-dimensional (3D) coordinate system. The system controller device 110 may then determine that the location of the ball or player is the location (or near the location) of a particular recreational grounds monitoring robot 112, based on receiving a signal from that particular recreational grounds monitoring robot 112 indicative of the ball or player being detected by that recreational grounds monitoring robot 112. The system controller device 110 may then determine a game score and/or other game play statistics based on the determined location of the ball or player.

The electronic signal indicative of the ball or player being detected by the recreational grounds monitoring robot 112 may be received based on data generated and/or received by a laser scanning system (e.g., a LiDAR or structured light system) or camera of the recreational grounds monitoring robot 112. The system controller device 110, player mobile device 106, scoreboard device 104 and/or another device 114 may also display data and/or game statistics based on receiving a tracking signal from the one or more recreational grounds monitoring robots 112 as a result of the one or more recreational grounds monitoring robots 112 autonomously tracking, during game play, a current location of the ball or player detected by the one or more recreational grounds monitoring robots 112. The system controller device 110 and/or one or more recreational grounds monitoring robots 112 may also send, via communication system 108, control signals to one or more of the networked recreational grounds monitoring robots 112 in response to the received first electronic signal indicative of a ball or player being detected by one or more of the networked recreational grounds monitoring robots 112. The control signal may cause one or more of the networked recreational grounds monitoring robots 112 to move to track movement of the detected ball or player on the recreational ground during game play.

As one example, the system controller device 110 may determine a distance from the golf ball on a golf course to a known location of a tee-off area, a known location of a golf hole on the golf course, and/or some other target or location on the golf course known to the system controller device 110. This information may then be used by the system controller device 110 to compile and communicate game play statistics such as driving distance and accuracy scores. The system controller device 110 may also generate a 2D or 3D rendering, or topographical map, of the golf course, and indicate on the rendering or map the corresponding determined location of the golf ball on the golf course. In some embodiments, the system controller device 110 may determine a golf score based on how many times a new location of the golf ball is determined to occur within a particular time period of game play (counting each movement of the ball over a threshold distance on the golf course as a swing that hit the golf ball). These operations to determine a distance and compile and communicate information regarding game scores and game play statistics may also or instead be performed by one or more of the recreational grounds monitoring robots 112.

Such information regarding game scores and game play statistics may be communicated, via communication system 108, to the scoreboard device 104, player mobile device 106 and/or other device 114, from the system controller device 110 and/or directly from one or more of the recreational grounds monitoring robots 112. The scoreboard device 104, player mobile device 106 and/or other device 114 may then present such information on a respective display of the scoreboard device 104, player mobile device 106 and/or other device 114. The scoreboard device 104 may present a graphical display of usage patterns, general course statistics and/or weekly leader board statistics based on the determined locations of players' golf balls on the golf course at particular times and triggering events. For example, items such as average driving distance, total distance the ball is driven over time or per game, accuracy statistics regarding how frequently the ball lands on the fairway, how close the ball is to the fairway or other target areas, comparative statistics to other players, etc., may be presented on the scoreboard device 104, player mobile device 106 and/or other device 114.

Examples of the other device 114 may include, but are not limited to, a presentation device, a television ("TV"), a mobile device, a smartphone, a tablet device, a personal computer ("PC"), a sound system receiver, a digital video recorder ("DVR"), a digital video disc ("DVD") device, game system, or the like. The scoreboard device 104, player mobile device and/or other device 114 may employ a display, one or more speakers, and/or other output devices to communicate video and/or audio content to a user. In many implementations, the scoreboard device 104, player mobile device 106 and/or other device 114 are communicatively coupled, directly or indirectly, to the recreational grounds monitoring robots 112. Further, the system controller device 110, scoreboard device 104, player mobile device 106 and/or other device 114 may be integrated into a single device. Such a single device may have the above-described functionality of the system controller device 110, scoreboard device 104, player mobile device 106 and/or other device 114, or may even have additional functionality.

Information regarding or based on the determined location of the ball or player may be communicated to the system controller device 110, scoreboard device 104, player mobile device 106 and/or other device 114 from the recreational grounds monitoring robots 112 through suitable communication media, generally illustrated as communication system 108 for convenience. Communication system 108 may include many different types of communication media, now known or later developed. Non-limiting media examples include telephone systems, the Internet, internets, intranets, cable systems, fiber optic systems, microwave systems, asynchronous transfer mode ("ATM") systems, frame relay systems, digital subscriber line ("DSL") systems, radio frequency ("RF") systems, and satellite systems. Communication system 108 may include any telecommunications network, computer network, or combination of telecommunications and computer networks that enables applicable communication between the various devices connected to the communication system 108 shown in FIG. 1. For example, a communications network of communication system 108 may include a local area network that uses wireless fidelity (Wi-Fi) high frequency radio signals to transmit and receive data over distances of a few hundred feet. The local area network may be a wireless local area network (WLAN) based on the Institute of Electric and Electronic Engineers (IEEE) 802.11 standards. However, other wired and wireless communications networks and protocols may be used to link the various devices and systems shown in FIG. 1. Thus, systems shown in FIG. 1 may have various applicable wireless transmitters and receivers and, in the case of using a Wi-Fi wireless link, may also have the corresponding executable Wi-Fi compatible network communications software that initiates, controls, maintains or manages the wireless link between the systems shown in FIG. 1 and the various other devices and systems within, or communication system 108 over the Wi-Fi signal of communication system 108.

The communication system 108 may comprise connections to the systems shown in FIG. 1 that provide services to the systems shown in FIG. 1, and may itself represent multiple interconnected networks. For instance, wired and wireless enterprise-wide computer networks, intranets, extranets, and/or the Internet may be included in, or comprise a part of, communication system 108. Embodiments may include various types of communication networks including other telecommunications networks, cellular networks and other mobile networks. There may be any variety of computers, switching devices, routers, bridges, firewalls, edge devices, multiplexers, phone lines, cables, telecommunications equipment and other devices within communication system 108 and/or in the communications paths between the recreational grounds monitoring robots 112, player mobile device 106, scoreboard device 104, other device 114 and/or system controller device 110. Some or all of such equipment of communication system 108 may be owned, leased or controlled by third-party service providers.

In accordance with an aspect of the disclosure, the recreational grounds monitoring robot 112, player mobile device 106, scoreboard device 104, other device 114 and/or system controller device 110 may contain discrete functional program modules that might make use of an application programming interface (API), or other object, software, firmware and/or hardware, to request services of each other (e.g., ball or player location and soil moisture data services) and/or one or more of the other entities within or connected to the communication system 108.

For example, communication can be provided over a communications medium, e.g., client and server systems running on any of the recreational grounds monitoring robots 112, player mobile device 106, scoreboard device 104, other device 114 and/or system controller device 110. These client and server systems may be coupled to one another via transmission control protocol/internet protocol (TCP/IP) connection(s) for high-capacity communication. The "client" is a member of a class or group that uses the services (e.g., ball or player location and soil moisture data services) of another class or group to which it is not related. In computing, a client is a process, i.e., roughly a set of instructions or tasks, executed by hardware that requests a service provided by another program. Generally, the client process utilizes the requested service without having to "know" any working details about the other program or the service itself. In a client/server architecture, particularly a networked system, a client is usually a computer or device that accesses shared network resources provided by another computer or device, e.g., a server. In the example of FIG. 1, the system controller device 110 may be a client requesting the services of the recreational grounds monitoring robots 112, and the player mobile device 106, scoreboard device 104 and/or other device 114 may be clients requesting the services of the system controller device 110 and/or the recreational grounds monitoring robots 112 acting as server(s). However, any entity in FIG. 1, including the recreational grounds monitoring robots 112, player mobile device 106, scoreboard device 104, system controller device 110 and other device 114, can be considered a client, a server, or both, depending on the circumstances.

One or more cellular towers and stations may be part of a cellular network that is part of the communication system 108 and may be communicatively linked by one or more communications networks or communication mediums within the communication system 108 (e.g., using a cellular or other wired or wireless signal) in order to facilitate sending and receiving information in the form of synchronous or asynchronous data. This communication may be over a wireless signal on the cellular network of communication system 108 using applicable combinations and layers of telecommunications and networking protocols and standards such as fourth generation broadband cellular network technology (4G), Long Term Evolution (LTE), HTTP and TCP/IP, etc.

Although the physical environment of communication system 108, including the recreational grounds monitoring robot 112, player mobile device 106, scoreboard device 104, other device 114 and/or system controller device 110, may have connected devices such as computers, the physical environment may alternatively have, or be described as comprising, various digital devices such as smartphones, tablets, personal digital assistants (PDAs), televisions, MP3 players, etc.; software objects such as interfaces, Component Object Model (COM) objects; and the like.

There are a variety of systems, components, and network configurations that may also support distributed computing and/or cloud-computing environments within the communication system 108. For example, computing systems may be connected together within the communication system 108 by wired or wireless systems, by local networks or by widely distributed networks. Many networks may be coupled to the Internet, which provides an infrastructure for widely distributed computing, and encompasses many different networks. Any such infrastructures, whether coupled to the Internet or not, may be used in conjunction with, be connected to, or comprise part of the communication system 108.

Although not required, the embodiments will be described in the general context of computer-executable instructions, such as program application modules, objects, or macros stored on computer- or processor-readable storage media and executed by a computer or processor. Those skilled in the relevant art will appreciate that the illustrated embodiments as well as other embodiments can be practiced with other system configurations and/or other computing system configurations, including hand-held devices, multiprocessor systems, microprocessor-based or programmable consumer electronics, personal computers ("PCs"), network PCs, minicomputers, mainframe computers, and the like. The embodiments can be practiced in distributed computing environments where tasks or modules are performed by remote processing devices, which are linked through a communications network such as communication system 108. In a distributed computing environment, program modules may be located in both local and remote memory storage devices.

In at least one embodiment, the received signals from the ball or player detector of each recreational grounds monitoring robot 112 is converted by the recreational grounds monitoring robot 112 into a suitable signal that is ultimately communicated to the player mobile device 106, scoreboard device 104, system controller device 110 and/or other device 114. Other embodiments of the player mobile device 106, scoreboard device 104, system controller device 110 and/or other device 114 may receive such signals from recreational grounds monitoring robots 112 via locally broadcast RF signals, cable, fiber optic, Internet media, or the like.

In addition, system controller device 110 may provide various forms of content and/or services to various devices. For example, system controller device 110 may also provide information to the player mobile device 106, scoreboard device 104, and/or other device 114 including or regarding historical game play statistics, commentary, comparative game play statistics (driving distances, etc.) to other players who have played on the same hole or course (including professional players) video of game play, images of game play, images of the ball at its current location, weather data, and other sports and entertainment multimedia content. System controller device 110 may provide an electronic program guide or other menu system data or software for a user of the recreational grounds monitoring robot 112 to organize, navigate and select soil moisture levels and related information, available game play statistics that were received based on the determined location of the ball or player and other content.

The above description of the environment 102, and the various devices therein, is intended as a broad, non-limiting overview of an example environment in which various embodiments of systems and methods for grounds monitoring may be implemented. FIG. 1 illustrates just one example of an environment 102, and the various embodiments discussed herein are not limited to such environments. In particular, environment 102, and the various devices therein, may contain other devices, systems and/or media not specifically described herein.

Example embodiments described herein provide applications, tools, data structures and other support to implement systems and methods for grounds monitoring. Other embodiments of the described techniques may be used for various purposes, including, but not limited to, location of other objects on recreational grounds, parks, fields, and other areas that use moisture sensors or other sensors distributed throughout the applicable area. In the following description, numerous specific details are set forth, such as data formats, program sequences, processes, and the like, in order to provide a thorough understanding of the described techniques. The embodiments described also can be practiced without some of the specific details described herein, or with other specific details, such as changes with respect to the ordering of the code flow, different code flows, and the like. Thus, the scope of the techniques and/or functions described are not limited by the particular order, selection, or decomposition of steps described with reference to any particular module, component, or routine.

Figure 2:
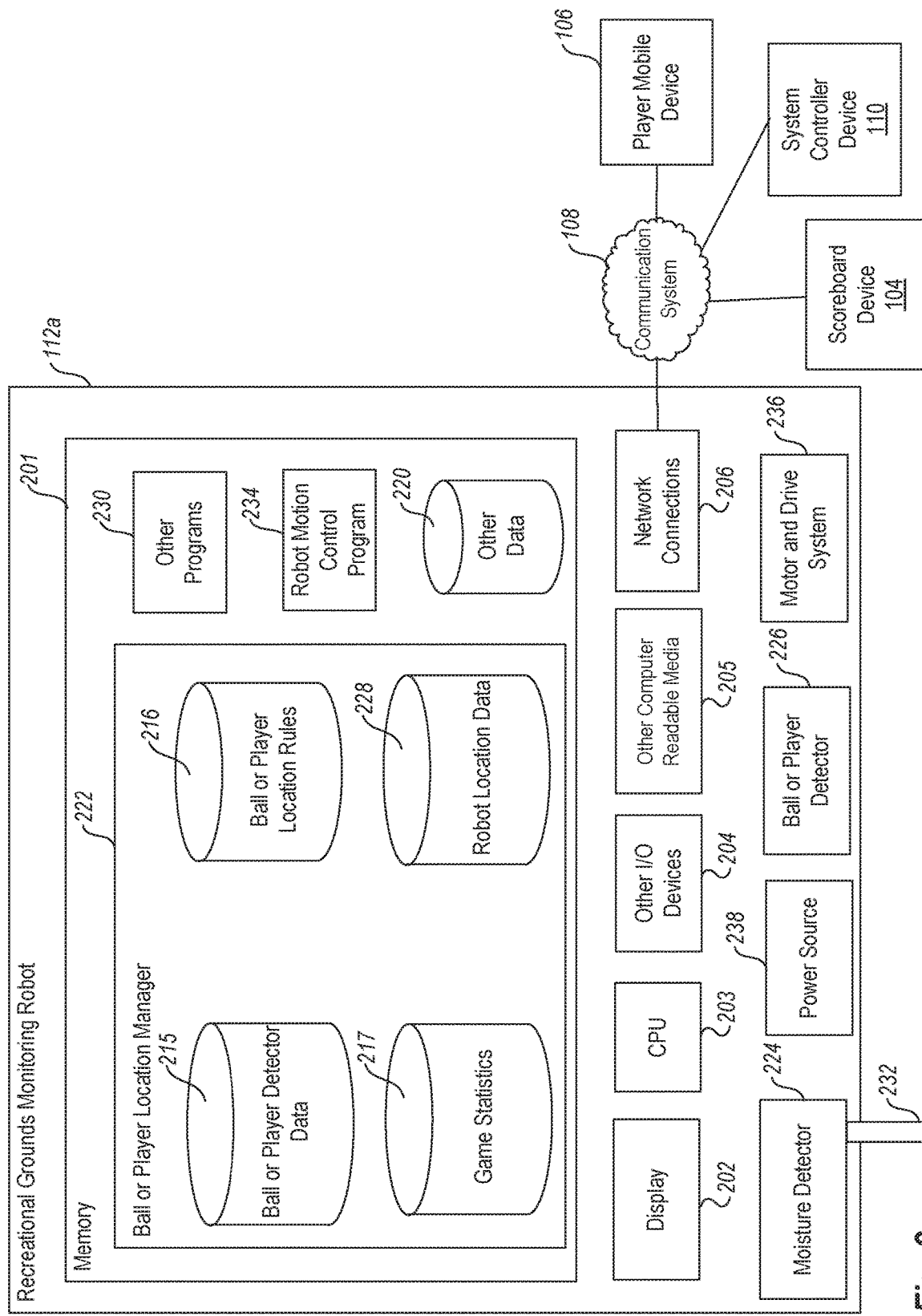
FIG. 2 is a block diagram illustrating elements of an example recreational grounds monitoring robot, according to one example embodiment.

FIG. 2 is a block diagram illustrating elements of an example recreational grounds monitoring robot 112a, according to one example embodiment.

In one embodiment, the recreational grounds monitoring robot 112a is a robotic device powered by a power source 238, such as a rechargeable battery or other mobile power source. The recreational grounds monitoring robot 112a includes a moisture detector 224 coupled to one or more soil probe instruments, such as soil probe 232, that may measure the volumetric water content indirectly by using some property of the soil, such as electrical resistance, dielectric constant, or interaction with neutrons, as a proxy for the moisture content. The relation between the measured property and soil moisture is calibrated and may vary depending on environmental factors such as soil type, temperature, or electric conductivity. Reflected microwave radiation is affected by the soil moisture and may be used for remote sensing. Soil moisture sensors may refer to sensors that estimate volumetric water content. Another class of sensors measure another property of moisture in soils called water potential. These sensors are often referred to as soil water potential sensors, and include tensiometers and gypsum blocks in various embodiments. As used herein, reference to recreational grounds monitoring robots 112 also includes such sensors that measure water potential. The motor and drive system 236, which may be coupled to one or more central processing units ("CPU") 203, may control the motor and drive system to steer and move the wheels of the recreational grounds monitoring robot 112 according to the robot motion control program 234 and also deploy and retract the soil probe 232 at various locations on the recreational ground according to the robot motion control program 234.

The recreational grounds monitoring robot 112a also includes ball or player detector 226. The ball or player detector 226 is operable to detect a ball or player on the recreational ground or at a particular location on the recreational ground.

For example, this detection may be accomplished via one or more sensors described above and/or other systems that may comprise the ball or player detector 226, including but not limited to, one or more of: a video or still frame camera, object recognition system, laser scanning system (e.g., a light imaging, detection, and ranging (LiDAR) or scanning system), a motion sensor, a computer vision system, video tracking system, a three-dimensional (3D) pose estimation system, a machine learning system, an indexing system, a motion estimation system, an image restoration system and a scene reconstruction system. In some embodiments, the ball or player detector of the recreational grounds monitoring robot 112 may detect an object detected on the recreational ground as being a ball or particular player or particular team member, and may also determine where on the recreational ground the detected object is located. For example, the recreational grounds monitoring robot 112 may determine its own location via triangulation, trilateration, time difference of arrival and/or time of arrival ranging systems based on two or more transmitters on the recreational ground at known locations providing locational or beacon signals received by the recreational grounds monitoring robot 112. In some embodiments the recreational grounds monitoring robot 112 may also or instead use a global positioning system (GPS) of the recreational grounds monitoring robot 112 to determine its own location on the recreational ground.

Based on the current location of the recreational grounds monitoring robot 112 on the recreational ground when the object is detected, the direction the camera of the ball or player detector of the recreational grounds monitoring robot 112 is pointed when the object on the recreational ground is detected and the size of the object in the video or image captured by the recreational grounds monitoring robot 112 (to aid in determining distance of the object from the recreational grounds monitoring robot 112), the location on the recreational ground of the detected object may be determined using one or more of the detection systems that may comprise the ball or player detector. For example, a computer vision system of the ball or player detector may be used to reconstruct a 3D model of the scene depicted in one or more images of the object captured by the recreational grounds monitoring robot 112. One or more other images of the detected object captured at the same time by one or more other recreational grounds monitoring robots 112 at different known locations on the recreational ground may also be used to aid in the computer vision and/or triangulation process used to determine the location of the detected object by providing further data points to more accurately pinpoint the location of the object. In this manner, the detected object need not have built-in GPS or other object location technology for the recreational grounds monitoring robot 112, player mobile device 106 or system controller device 110 to determine where on the recreational ground the detected object is located. In some embodiments, detection of a ball on the recreational ground may be accomplished via one or more of a magnetometer, vibration detector and motion sensor of the ball or player detector 226.

Note that one or more general purpose or special purpose computing systems/devices may be used to operate the recreational grounds monitoring robot 112; cause the moisture detector 224 to detect a moisture level of the grass recreational ground; cause the ball or player detector 226 to detect a ball or player on the recreational ground; in response to the detection of the ball or player being detected by the recreational grounds monitoring robot 112a, generate a first electronic signal indicative of the ball or player being detected by the recreational grounds monitoring robot 112a; communicate the first electronic signal indicative of the ball or player being detected by the recreational grounds monitoring robot to the system controller device 110, player mobile device 106, and/or scoreboard device 104; store ball or player location rules in ball or player location rules storage 216; store ball or player detector data in ball or player detector data storage 215; store game statistics in game statistics storage 217; store recreational grounds monitoring robot location data in recreational grounds monitoring robot location data storage 228; store information regarding the recreational grounds monitoring robot 112a; store information regarding other recreational grounds monitoring robots 112 in other data storage 220; and communicate with the player mobile device 106, scoreboard device 104 and/or system controller device 110. Furthermore, each block shown may represent one or more such blocks as appropriate to a specific embodiment, or may be combined with other blocks. Also, the ball or player location manager 222 may be implemented in software, hardware, firmware, or in some combination to achieve the capabilities described herein.

In the embodiment shown, recreational grounds monitoring robot 112 also comprises a computer memory ("memory") 201, a display 202, one or more central processing units ("CPU") 203, input/output devices 204 (e.g., button panel, RF or infrared receiver, light emitting diode (LED) panel, liquid crystal display (LCD), USB ports, other communication ports, and the like), other computer-readable media 205, and network connections 206 (e.g., Wi-Fi interface(s), Bluetooth® interface, short range wireless interface, personal area network interface, Ethernet port(s), and/or other network ports). The input/output devices 204 devices may include one or more sensors, including but not limited to, one or more of: a video or still frame camera, object recognition system, laser scanning system (e.g., a light imaging, detection, and ranging (LiDAR) or scanning system), a motion sensor, a computer vision system, video tracking system, a three-dimensional (3D) pose estimation system, a machine learning system, an indexing system, a motion estimation system, an image restoration system and a scene reconstruction system. One or more such components that comprise the recreational grounds monitoring robot 112 may also comprise, as applicable, the one or more general purpose or special purpose computing systems/devices that may be used to operate one or more of the system controller device 110, player mobile device 106 and scoreboard device 104.

The ball or player location manager 222 is shown residing in memory 201. In other embodiments, some portion of the contents and some, or all, of the components of the ball or player location manager 222 may be stored on and/or transmitted over the other computer-readable media 205. The components of the recreational grounds monitoring robot 112 and ball or player location manager 222 preferably execute on one or more CPUs 203, and facilitate the receiving, decoding, processing, selecting, recording, playback and displaying of programming content one or more of the various formats described herein.

As described in more detail herein, the ball or player location manager 222 performs the functionality of the systems and methods for grounds monitoring, including, but not limited to: causing the moisture detector 224 to detect a moisture level of the grass recreational ground; causing the ball or player detector 226 to detect a ball or player on the recreational ground; in response to the detection of the ball or player being detected by the recreational grounds monitoring robot 112a, generating a first electronic signal indicative of the ball or player being detected by the recreational grounds monitoring robot 112a; communicating the first electronic signal indicative of the ball or player being detected by the recreational grounds monitoring robot to the system controller device 110, player mobile device 106, and/or scoreboard device 104; storing the ball or player location rules in ball or player location rules storage 216; storing ball or player detector data in ball or player detector data storage 215; storing game statistics in game statistics storage 217; storing recreational grounds monitoring robot location data in recreational grounds monitoring robot location data storage 228; storing other information regarding the recreational grounds monitoring robot 112a in other data storage 220; storing information regarding other recreational grounds monitoring robots 112 in other data storage 220; and communicating with the player mobile device 106, scoreboard device 104 and/or system controller device 110. For example, the ball or player location manager 222 may implement various ball or player location rules stored in ball or player location rules storage 216. Such ball or player location rules may indicate that, based on the current location of the recreational grounds monitoring robot 112 on the recreational ground when the object is detected, the direction the camera of the ball or player detector of the recreational grounds monitoring robot 112 is pointed when the object on the recreational ground is detected and the size of the object in the video or image captured by the recreational grounds monitoring robot 112 (to aid in determining distance of the object from the recreational grounds monitoring robot 112), the location on the recreational ground of the detected object may be determined using one or more of the detection systems that may comprise the ball or player detector 226. For example, a computer vision system implemented by the ball or player location manager 222 may be used to reconstruct a 3D model of the scene depicted in one or more images of the object captured by the ball or player detector 226 of the recreational grounds monitoring robot 112. One or more other images of the detected object captured at the same time by one or more other recreational grounds monitoring robots 112 at different known locations on the recreational ground may also be used by a particular recreational grounds monitoring robot 112 and/or system controller device 110 to aid in the computer vision and/or triangulation process used to determine the location of the detected object by providing further data points to more accurately pinpoint the location of the object. In this manner, the detected object need not have built-in GPS or other object location technology for the recreational grounds monitoring robot 112, player mobile device 106 or system controller device 110 to determine where on the recreational ground the detected object is located.

Such ball or player location rules may also indicate threshold values for magnetic signal strength of a ball as detected by a magnetometer of the ball or player detector 226, to be used to determine whether a ball is within proximity or within a "proximity zone" to the recreational grounds monitoring robot 112a, and/or magnetic field signatures of a ball as detected by a magnetometer of the ball or player detector 226, to be used to determine whether a ball is within proximity or within a "proximity zone" to the recreational grounds monitoring robot 112a. Other low power communication technologies, such as Bluetooth 4.0 (also referred to as Bluetooth® Low Energy or BLE) and ZigBee (with IEEE 802.15.4 as the physical network layer) may also or instead be used for proximity detection of the ball in various embodiments. Such ball or player location rules in ball or player location rules storage 216 may also include rules for game play based on the location of the ball or player relative to a particular recreational grounds monitoring robot 112a as detected by the ball or player detector 226. For example, during the play of a golf game, the ball or player location may be tracked via the ball or player detector 226 of a particular recreational grounds monitoring robot 112, or may be tracked via multiple recreational grounds monitoring robots 112 communicating with each other and working cooperatively to pass tracking of the ball or player to the particular recreational grounds monitoring robot 112 to which the ball or player is closest. The recreational grounds monitoring robot may also identify a particular player or team member via object recognition and/or facial recognition functionality of the ball or player location manager 222. In this manner, the recreational grounds monitoring robot 112 and/or system controller device 110 may collect game play statistics in game statistics storage 217 for each different player in the game without having to have the ball of each player communicate a unique code, signature or identification signal to differentiate the ball from a ball of another player in the same game. The game statistics storage 217 and/or the other data storage 220 may store data regarding historical game play statistics, commentary, comparative game play statistics (driving distances, etc.) to other players who have played on the same hole or course (including professional players), video of game play, images of game play, images of the ball at its current location and other game play data as described herein.

The recreational grounds monitoring robot location data in recreational grounds monitoring robot location data storage 228 may include data indicative of the location of the recreational grounds monitoring robot 112a and/or locations of other recreational grounds monitoring robots relative to each other and/or as coordinates (e.g., GPS coordinates) in a 2D or 3D coordinate system common to the recreational grounds monitoring robots 112. This recreational grounds monitoring robot location data may be used to determine the location on a recreational ground of a ball detected to be in proximity of a particular recreational grounds monitoring robot on the recreational ground, such as recreational grounds monitoring robot 112a. In some embodiments, more than one recreational grounds monitoring robot may detect the same ball or player on the recreational ground. In such a case, the ball or player location rules stored in the ball or player location rules storage 216 of the system controller device 110 may cause the system controller device 110 to determine the location of the ball or player on the recreational ground based on the strength of the signal received by the recreational grounds monitoring robot caused by the ball or player being detected by it, as compared to the strength of the signals received by one or more other recreational grounds monitoring robots caused by the ball also being within proximity of those recreational grounds monitoring robots 112 on the recreational ground. Such signal strength may also be used to estimate distance from each recreational grounds monitoring robot to the ball determined to be in proximity to the recreational grounds monitoring robot 112. The estimated distances from each recreational grounds monitoring robot to which the ball is determined to be in proximity may also be used by the system controller device 110 to triangulate the location of the ball or player on the recreational ground based on the recreational grounds monitoring robot location data communicated to the system controller device 110.

As described herein, the ball or player location manager 222 may interact via the communication system 108 with other devices. For example, the other device may be a home computing system (e.g., a desktop computer, a laptop computer, mobile device, etc.) that includes or has access to (e.g., via communication system 108) the functionality of the player mobile device 106, scoreboard device 104 and/or system controller device 110.

Other code or programs 230 (e.g., an audio/video processing module, a configuration/settings manager module, a Web server, and the like), and potentially other data repositories, such as data repository 220 for storing other data (user profiles, preferences and configuration data, etc.), also reside in the memory 201, and preferably execute on one or more CPUs 203. Of note, one or more of the components in FIG. 2 may or may not be present in any specific implementation. For example, some embodiments may not provide other computer-readable media 205 or a display 202.

In some embodiments, the recreational grounds monitoring robot 112a and ball or player location manager 222 include an application program interface ("API") that provides programmatic access to one or more functions of the recreational grounds monitoring robot 112 and ball or player location manager 222. For example, such an API may provide a programmatic interface to one or more functions of the ball or player location manager 222 that may be invoked by one of the other programs 230, player mobile device 106, scoreboard device 104 and/or system controller device 110, or some other module. In this manner, the API may facilitate the development of third-party software, such as user interfaces, plug-ins, adapters (e.g., for integrating functions of the ball or player location manager 222, scoreboard device 104 and system controller device 110 into desktop and mobile applications), and the like to facilitate ball or player location and game play as described herein on those various connected devices.

In an example embodiment, components/modules of the recreational grounds monitoring robot 112 and ball or player location manager 222 are implemented using standard programming techniques. For example, the ball or player location manager 222 may be implemented as a "native" executable running on the CPU 203, along with one or more static or dynamic libraries. In other embodiments, the recreational grounds monitoring robot 112 and ball or player location manager 222 may be implemented as instructions processed by a virtual machine that executes as one of the other programs 230. In general, a range of programming languages known in the art may be employed for implementing such example embodiments, including representative implementations of various programming language paradigms, including but not limited to, object-oriented (e.g., Java, C++, C#, Visual Basic.NET, Smalltalk, and the like), functional (e.g., ML, Lisp, Scheme, and the like), procedural (e.g., C, Pascal, Ada, Modula, and the like), scripting (e.g., Perl, Ruby, Python, JavaScript, VBScript, and the like), or declarative (e.g., SQL, Prolog, and the like).

In a software or firmware implementation, instructions stored in a memory configure, when executed, one or more processors of the recreational grounds monitoring robot 112 to perform the functions of the ball or player location manager 222. In one embodiment, instructions cause the CPU 203 or some other processor coupled to the moisture detector 224 and ball or player detector 226, such as an I/O controller/processor, to cause the recreational grounds monitoring robot 112a to detect a ball or player on the recreational ground.

The embodiments described above may also use other synchronous or asynchronous client-server computing techniques. However, the various components may be implemented using more monolithic programming techniques as well, for example, as an executable running on a single CPU computer system, or alternatively decomposed using a variety of structuring techniques known in the art, including but not limited to, multiprogramming, multithreading, client-server, or peer-to-peer, running on one or more computer systems each having one or more CPUs. Some embodiments may execute concurrently and asynchronously, and communicate using message passing techniques. Equivalent synchronous embodiments are also supported by a ball or player location manager 222 implementation. Also, other functions could be implemented and/or performed by each component/module, and in different orders, and by different components/modules, yet still achieve the functions of the recreational grounds monitoring robot 112 and the ball or player location manager 222.

In addition, programming interfaces to the data stored as part of the recreational grounds monitoring robot 112 and ball or player location manager 222, can be available by standard mechanisms such as through C, C++, C#, and Java APIs; libraries for accessing files, databases, or other data repositories; scripting languages such as XML; or Web servers, FTP servers, or other types of servers providing access to stored data. The ball or player location rules in ball or player location rules storage 216, ball or player detector data in ball or player detector data storage 215, game statistics in game statistics storage 217 and recreational grounds monitoring robot location data in recreational grounds monitoring robot location data storage 228 may be implemented as one or more database systems, file systems, or any other technique for storing such information, or any combination of the above, including implementations using distributed computing techniques.

Different configurations and locations of programs and data are contemplated for use with techniques described herein. A variety of distributed computing techniques are appropriate for implementing the components of the illustrated embodiments in a distributed manner including but not limited to TCP/IP sockets, RPC, RMI, HTTP, and Web Services (XML-RPC, JAX-RPC, SOAP, and the like). Other variations are possible. Other functionality could also be provided by each component/module, or existing functionality could be distributed amongst the components/modules in different ways, yet still achieve the functions of the ball or player location manager 222.

Furthermore, in some embodiments, some or all of the components of the recreational grounds monitoring robot 112, the player mobile device 106, the scoreboard device 104 and the ball or player location manager 222 may be implemented or provided in other manners, such as at least partially in firmware and/or hardware, including, but not limited to one or more application-specific integrated circuits ("ASICs"), standard integrated circuits, controllers (e.g., by executing appropriate instructions, and including microcontrollers and/or embedded controllers), field-programmable gate arrays ("FPGAs"), complex programmable logic devices ("CPLDs"), and the like. Some or all of the system components and/or data structures may also be stored as contents (e.g., as executable or other machine-readable software instructions or structured data) on a computer-readable medium (e.g., as a hard disk; a memory; a computer network, cellular wireless network or other data transmission medium; or a portable media article to be read by an appropriate drive or via an appropriate connection, such as a DVD or flash memory device) so as to enable or configure the computer-readable medium and/or one or more associated computing systems or devices to execute or otherwise use, or provide the contents to perform, at least some of the described techniques. Some or all of the system components and data structures may also be stored as data signals (e.g., by being encoded as part of a carrier wave or included as part of an analog or digital propagated signal) on a variety of computer-readable transmission mediums, which are then transmitted, including across wireless-based and wired/cable-based mediums, and may take a variety of forms (e.g., as part of a single or multiplexed analog signal, or as multiple discrete digital packets or frames). Such computer program products may also take other forms in other embodiments. Accordingly, embodiments of this disclosure may be practiced with other computer system configurations.

Figure 3:
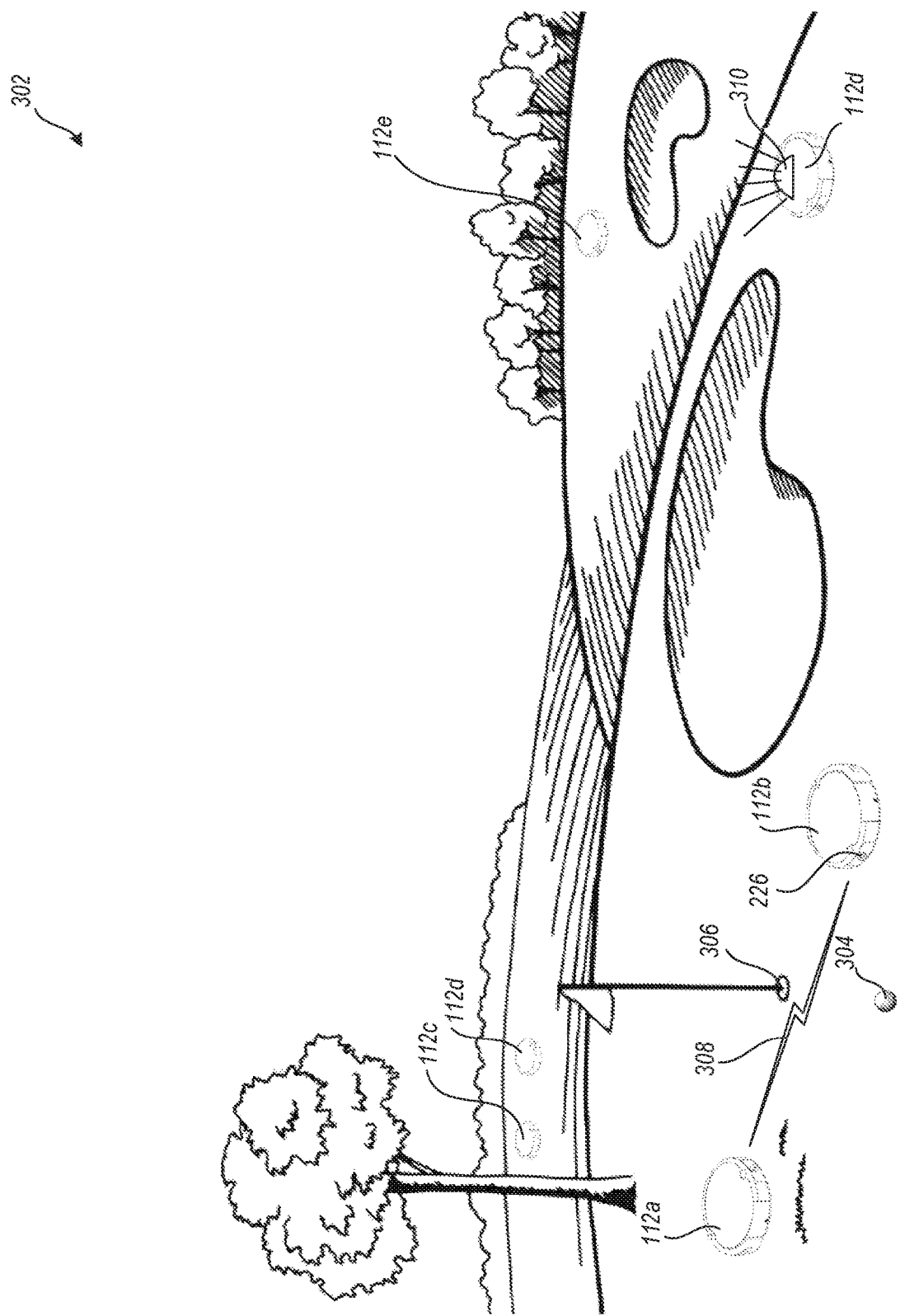
FIG. 3 is an illustration of an example golf course with a plurality of networked recreational grounds monitoring robots distributed thereon, according to one example embodiment.

FIG. 3 is an illustration of a portion of an example recreational ground 302, which is a recreational ground 302 in the present example shown in FIG. 3, with a plurality of networked recreational grounds monitoring robots 112 distributed thereon, according to one example embodiment. The number of recreational grounds monitoring robots 112 may vary and may be fewer or more than those illustrated in FIG. 3. Shown at various locations on the recreational ground 302 are recreational grounds monitoring robot 112a, recreational grounds monitoring robot 112b, recreational grounds monitoring robot 112c, recreational grounds monitoring robot 112d and recreational grounds monitoring robot 112e. Generally, the larger the number of networked recreational grounds monitoring robots 112 distributed on the recreational ground 302, the more accurate the location of objects on the recreational ground 302, such as the golf ball 304 or a player (not shown) may be determined and tracked using such recreational grounds monitoring robots 112.

The recreational grounds monitoring robots 112 may move about the recreational ground 302 measuring soil moisture at various selectable locations, performing security monitoring and/or identifying and tracking objects on the recreational ground 302, such as players, golf carts and golf balls, The recreational grounds monitoring robot 112 may move about the recreational ground, in a selectable pre-set pattern or a random pattern, stopping at various points to measure soil moisture and perform other soil and grass tests and measurements. The recreational grounds monitoring robots 112 may also have charging or docking stations (not shown) along the boundaries or edges of the recreational ground 302 to which they may autonomously return at regular intervals, designated time periods or when a particular recreational grounds monitoring robot 112 detects the battery is below a threshold level of charge.

In some embodiments, the recreational grounds monitoring robot 112 moves about the recreational ground 302 in a pre-set pattern using, or otherwise based on, a stored representation of a map of the golf course, which may be stored on other data storage 220 (shown in FIG. 2). Whether moving about autonomously in a random or pre-set pattern, the robot motion control program 234 of the recreational grounds monitoring robot 112 may also detect obstacles and potential hazards to the recreational grounds monitoring robot 112 and, in response, implement corresponding contingency movements to avoid such obstacles and potential hazards.

For example, the recreational grounds monitoring robot 112 may detect such obstacles and potential hazards using sensors that comprise the ball or player detector 226 or other I/O devices 204 (shown in FIG. 2). Such sensors may include, but are not limited to, one or more of: cameras, motion sensors, vibration sensors, light sensors, accelerometers, tilt sensors, microphones, laser scanning devices or systems, LiDAR sensors, antennae, structured light sensors, touch sensors, bump sensors, range finding sensors, infrared sensors, radio frequency range sensors, sonar devices, sound range finding devices, radar devices, electronically scanned RADAR (ESR) devices, night vision sensors, depth perception sensors, stereoscopic vision systems, temperature sensors, magnetometers, location sensors, GPS devices, audio detectors, soil moisture sensors, moisture detectors, humidity sensors, and chemical sensors. Such sensors may also be used in conjunction with one or more computer vision, scene reconstruction and/or location finding systems described herein to determine the current location of the robot relative to other objects in the recreational ground 302 including potential obstacles and hazards. For example, the recreational grounds monitoring robot 112b may detect a ball or player on the recreational ground 302 to be in the potential path of the recreational grounds monitoring robot 112b, and adjust the movement of the recreational grounds monitoring robot 112b accordingly to avoid the detected ball or player.

The selectable pre-set path on the recreational ground for the recreational grounds monitoring robot 112 may include stops at various locations on the recreational ground 302 to determine soil moisture levels using the moisture detector 224 (shown in FIG. 2), inspect the recreational ground 302 and/or take other tests or soil measurements. Using the camera, object recognition, range finding, location finding, facial recognition and/or other associated systems described herein, the recreational grounds monitoring robot 112 may also perform security monitoring of the recreational ground 302. For example, the recreational grounds monitoring robot 112 may recognize an object as an unauthorized person, and track their movement to an unauthorized area of the recreational ground 302. This may result in the recreational grounds monitoring robot 112 generating and communicating an alert including the detected location of the detected unauthorized person. In some embodiments, the recreational grounds monitoring robot 112 may identify a person as an unauthorized individual by comparing images of that person to stored reference images of all people authorized to be on the recreational ground 302. In some embodiments, individuals authorized to be on the recreational ground or at a particular location on the recreational ground may carry a wireless security token that emits an authenticated code or signal that the recreational grounds monitoring robot 112 may verify to determine whether the object detected to be a person is an individual authorized to be at the particular determined location on the recreational ground 302.

The recreational grounds monitoring robots may be in communication with one or more of a system controller device 110, scoreboard device 104 and/or player mobile device 106, such as via communication system 108 shown in FIG. 1 and FIG. 2. In some embodiments, the recreational grounds monitoring robots 112 may be in communication with each other directly, such as via a peer-to-peer wireless communication signal 308, and/or via communication system 108. Each recreational grounds monitoring robot may have a unique identification number or code associated with it along with data identifying a current location of the recreational grounds monitoring robot on the recreational ground 302. Such data may be communicated from each recreational grounds monitoring robot to one or more of the system controller device 110, the scoreboard device 104 and/or the player mobile device 106.

In the example shown in FIG. 3, during a round of golf, a golfer has hit a golf ball 304 toward the hole 306. The golf ball has landed in proximity to one or more of recreational grounds monitoring robot 112a and recreational grounds monitoring robot 112b. The known location of recreational grounds monitoring robot 112a, and recreational grounds monitoring robot 112b may be used to determine the location on the golf course of the ball 304 detected to be in proximity of recreational grounds monitoring robot 112a and/or recreational grounds monitoring robot 112b. In some embodiments, more than one recreational grounds monitoring robot may detect the same ball or player at the same time. For example, recreational grounds monitoring robot 112a, and recreational grounds monitoring robot 112b may each detect the ball 304 to be in proximity to it. In such a case, the system controller device 110 may determine the location of the ball 304 on the golf course based on the strength of the signal 308 received by recreational grounds monitoring robot 112a caused by the ball or player being detected by it as compared to the strength of the signal received by recreational grounds monitoring robot 112b caused by the ball also being within proximity of it. Such signal strength may also be used to estimate distances from recreational grounds monitoring robot 112a and recreational grounds monitoring robot 112b to which the ball is determined to be in proximity. The estimated distances from recreational grounds monitoring robot 112a and recreational grounds monitoring robot 112b to which the ball is determined to be in proximity may also be used by the system controller device 110 to determine the location of the ball or player on the golf course based on the known locations of recreational grounds monitoring robot 112a, recreational grounds monitoring robot 112b and which direction the camera or angle of view of each recreational grounds monitoring robot 112a and recreational grounds monitoring robot 112b communicated to the system controller device 110.

In some embodiments, one or more of the recreational grounds monitoring robots 112, such as recreational grounds monitoring robot 112d, and the robot motion control program 234 may cause the motor and drive system 236 to autonomously move the recreational grounds monitoring robot 112d around the recreational ground 302 as a target for a player to catch or hit with a ball as part of augmented game play or training. A target indicator 310, such as a light, marking or other identifier may be operably coupled to the recreational grounds monitoring robot 112d such that a player may easily identify and target the recreational grounds monitoring robot 112d. The recreational grounds monitoring robot 112d may then detect a particularly marked or tagged ball or a particular player in proximity to the recreational grounds monitoring robot 112d and store data of such detection to update a score or other game statistics accordingly.

Figure 4:
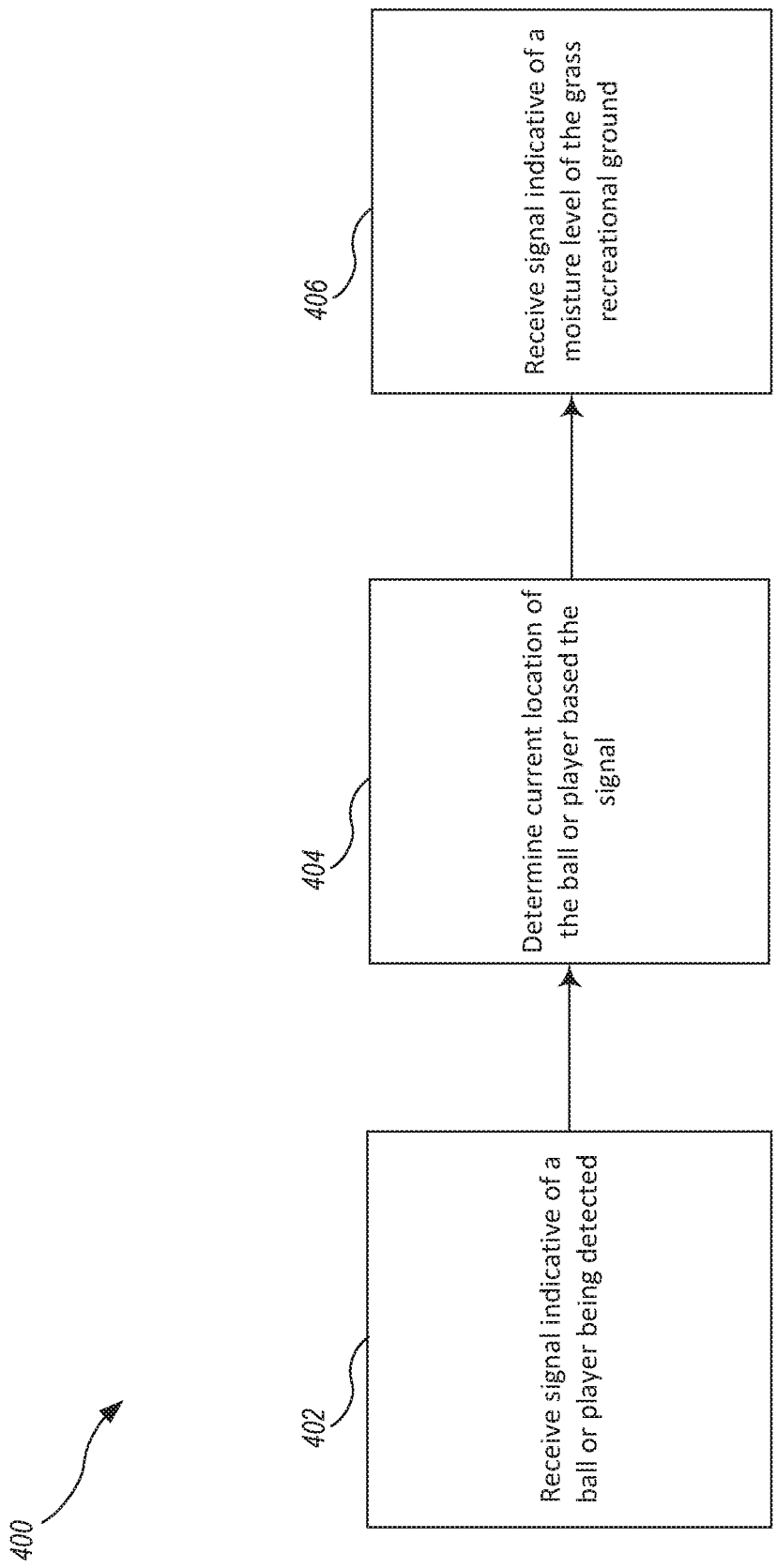
FIG. 4 is a diagram of a method for grounds monitoring, according to an example embodiment.

FIG. 4 is a diagram of a method 400 for grounds monitoring, according to an example embodiment.

At 402, the system controller device 110 receives a first electronic signal from at least one of a plurality of networked recreational grounds monitoring robots 112 distributed on a grass recreational ground 302. The first electronic signal is indicative of a ball or player being detected by the at least one of the plurality of networked recreational grounds monitoring robots 112.

At 404, the system controller device 110 determines a current location of the ball or player based on the first electronic signal indicative of the ball or player being detected by the at least one of the plurality of networked recreational grounds monitoring robots 112.

At 406, the system controller device 110 receives a second electronic signal from the least one of the plurality of networked recreational grounds monitoring robots 112 from which the first electronic signal indicative of the ball or player being detected by the at least one of the plurality of networked recreational grounds monitoring robots 112 was received. The second electronic signal is indicative of a moisture level of the grass recreational ground 302.

Figure 5:
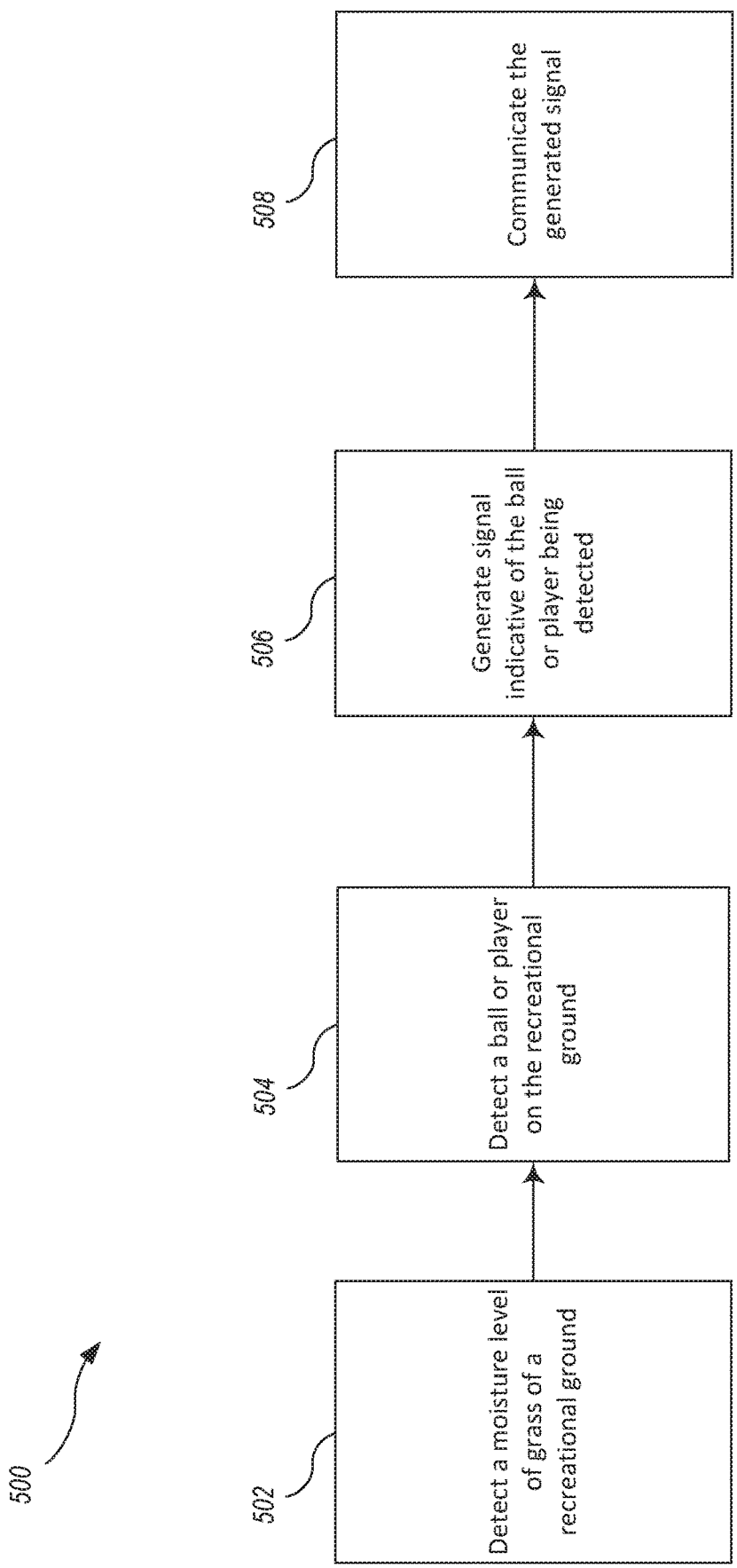
FIG. 5 is a diagram of a method for grounds monitoring, according to another example embodiment.

FIG. 5 is a diagram of a method 500 for grounds monitoring, according to another example embodiment.

At 502, the moisture detector 224 of the recreational grounds monitoring robot 112 detects a moisture level of grass of a recreational ground 302.

At 504, the ball or player detector 226 of the recreational grounds monitoring robot 112 detects a ball or player on the recreational ground during game play.

At 506, in response to the detection of the ball or player by the recreational grounds monitoring robot 112, the recreational grounds monitoring robot 112 generates a first electronic signal indicative of the ball or player being detected by the recreational grounds monitoring robot 112.

At 508, the recreational grounds monitoring robot 112 communicates the first electronic signal indicative of the ball or player being detected by the recreational grounds monitoring robot 112 to a system controller device 110.

Figure 6:
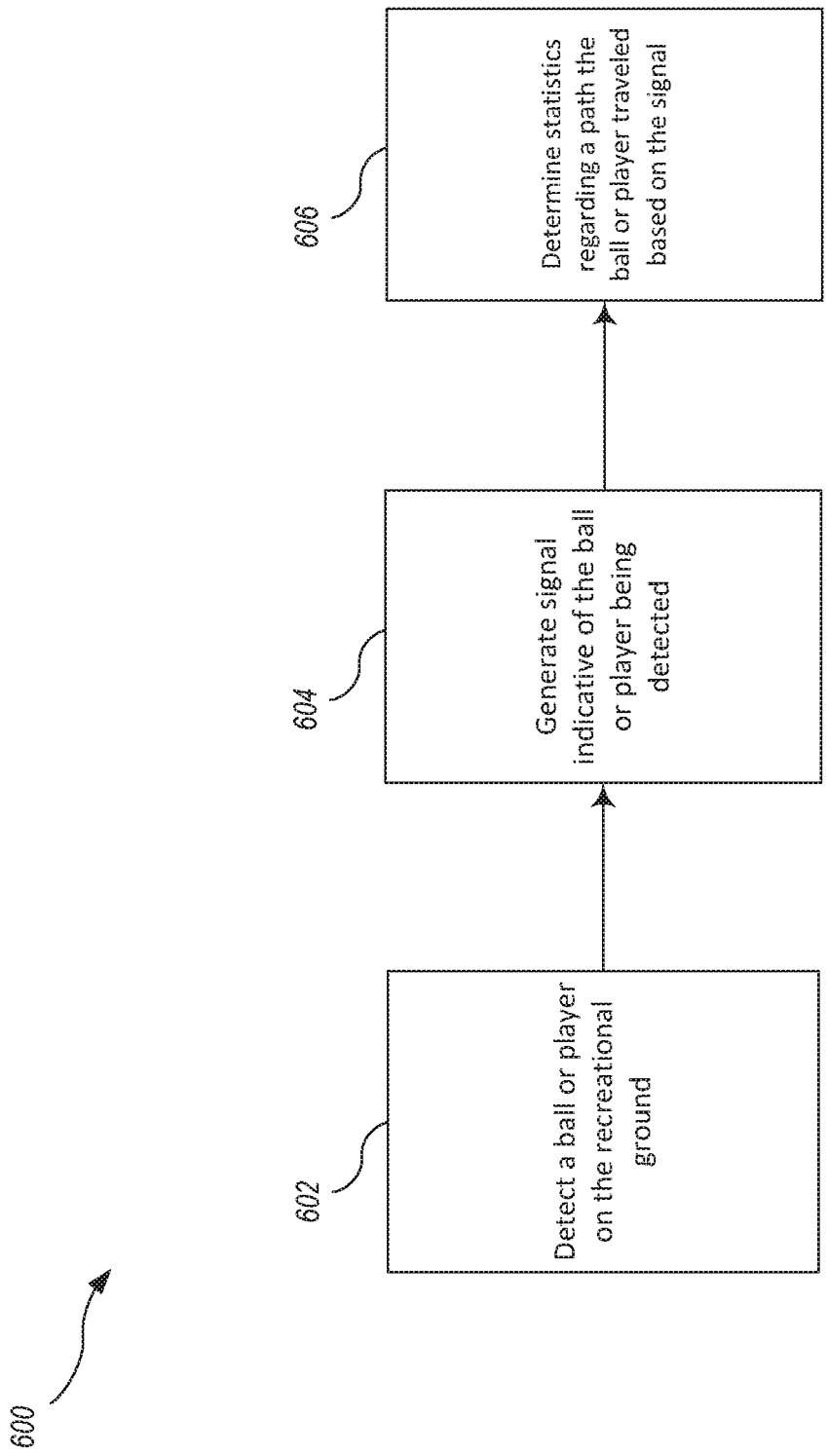
FIG. 6 is a diagram of a method of determining statistics regarding a path a ball or player traveled on a recreational ground, according to an example embodiment.

FIG. 6 is a diagram of a method 600 of determining statistics regarding a path a ball or player traveled on a recreational ground 302, according to an example embodiment.

At 602, the recreational grounds monitoring robot 112 detects a ball or player on the recreational ground during game play on the recreational ground. In some embodiments, this detection may occur while the recreational grounds monitoring robot 112 is located outside a playing area on the recreational ground 302.

At 604, the recreational grounds monitoring robot 112 generates the electronic signal indicative of the ball or player being detected by the recreational grounds monitoring robot 112.

At 606, the recreational grounds monitoring robot 112 determines statistics regarding a path the ball traveled during a game being played on the grass of the recreational ground 302. In some embodiments, the recreational grounds monitoring robot 112 or the system controller device 110 may receive additional electronic signals from each recreational grounds monitoring robot of the plurality of recreational grounds monitoring robots on the recreational ground. The additional electronic signals may include, for each recreational grounds monitoring robot of the plurality of networked recreational grounds monitoring robots, a respective electronic signal indicative of the ball or player being detected by the recreational grounds monitoring robot. The recreational grounds monitoring robot 112 or system controller device 110 may then determine statistics regarding a path the ball traveled during a game being played on the recreational ground 302 based on the received additional electronic signals from each recreational grounds monitoring robot of the plurality of recreational grounds monitoring robots.

While various embodiments have been described hereinabove, it is to be appreciated that various changes in form and detail may be made without departing from the spirit and scope of the invention(s) presently or hereafter claimed.

The invention claimed is:

1. A computer-implemented method, comprising:
receiving, by at least one computer processor, a first electronic signal from at least one of a plurality of networked recreational grounds monitoring robots distributed on a grass recreational ground, the first electronic signal indicative of a ball or player being detected by the at least one of the plurality of networked recreational grounds monitoring robots; and
determining, by at least one computer processor, a current location of the ball or player based on the first electronic signal indicative of the ball or player being detected by the at least one of the plurality of networked recreational grounds monitoring robots; and
receiving, by at least one computer processor, a second electronic signal from the least one of the plurality of networked recreational grounds monitoring robots from which the first electronic signal indicative of the ball or player being detected by the at least one of the plurality of networked recreational grounds monitoring robots was received, the second electronic signal indicative of a moisture level of the grass recreational ground.

2. The method of claim 1, further comprising communicating, by at least one computer processor, information based on the determined current location of the ball or player to at least one of: a device associated with a player of a game being played on the grass recreational ground and a device associated with providing statistics regarding the game being played on the grass recreational ground.

3. The method of claim 1, further comprising facilitating, by at least one computer processor, game play of a game currently being played on the grass recreational ground based on the determined current location of the ball or player.

4. The method of claim 1, wherein the first electronic signal indicative of the ball or player being detected by the at least one of the plurality of networked recreational grounds monitoring robots is received via a laser scanning system and camera of the at least one of the plurality of networked recreational grounds monitoring robots.

5. The method of claim 1, further comprising:
receiving a tracking signal from the at least one of the plurality of networked recreational grounds monitoring robots as a result of the at least one of the plurality of networked recreational grounds monitoring robots autonomously tracking, during game play, a current location of the ball or player detected by the at least one of the plurality of networked recreational grounds monitoring robots.

6. The method of claim 1, further comprising:
sending, by at least one computer processor, at least one control signal to the at least one of the plurality of networked recreational grounds monitoring robots in response to the received first electronic signal indicative of a ball or player being detected by the at least one of the plurality of networked recreational grounds monitoring robots, the control signal causing the at least one of the plurality of networked recreational grounds monitoring robots to move to track movement of the detected ball or player on the grass recreational ground during game play.

7. The method of claim 1, further comprising:
receiving, by at least one computer processor, additional electronic signals from each recreational grounds monitoring robot of the plurality of networked recreational grounds monitoring robots, the additional electronic signals including, for each recreational grounds monitoring robot of the plurality of networked recreational grounds monitoring robots, a respective electronic signal indicative of the ball or player being detected by the recreational grounds monitoring robot; and
determining statistics regarding a path the ball or player traveled during a game being played on the grass recreational ground based on the received additional electronic signals from each recreational grounds monitoring robot of the plurality of networked recreational grounds monitoring robots.

8. The method of claim 7, further comprising:
determining a distance the ball or player traveled during a game being played on the grass recreational ground based on the received additional electronic signals from each recreational grounds monitoring robot of the plurality of networked recreational grounds monitoring robots using a location of the at least one of the plurality of networked recreational grounds monitoring robots and the first electronic signal indicative of the ball or player being detected by the at least one of the plurality of networked recreational grounds monitoring robots.

9. The method of claim 1, further comprising determining, by at least one computer processor, a score of a game currently being played on the grass recreational ground based on the determined current location of the ball or player using a location of the at least one of the plurality of networked recreational grounds monitoring robots and the first electronic signal indicative of the ball or player being detected by the at least one of the plurality of networked recreational grounds monitoring robots.

10. The method of claim 1, further comprising determining, by at least one computer processor, a distance from the ball or player to a target during a game currently being played on the grass recreational ground based on the determined current location of the ball or player using a location of the at least one of the plurality of networked recreational grounds monitoring robots and the first electronic signal indicative of the ball or player being detected by the at least one of the plurality of networked recreational grounds monitoring robots.

11. The method of claim 1 wherein the grass recreational ground comprises a golf course, the ball is a golf ball and further comprising:
determining, by at least one computer processor, based on a determined current location of the golf ball using the first electronic signal indicative of the ball or player being detected by the at least one of the plurality of networked recreational grounds monitoring robots, one or more of: a driving distance of the golf ball; a location of the golf ball on the golf course; whether the golf ball is on a fairway of the golf course; whether the golf ball is on a putting green of the golf course; distance from the golf ball to a hole on the golf course; identification of the golf ball from a plurality of golf balls on the golf course; a golf score of a golfer associated with the golf ball; which hole on the golf course the golf ball is nearest; and which golf ball of a plurality of golf balls on the golf course is closest to a hole on the golf course.

12. A recreational grounds monitoring robot, comprising:
at least one processor;
at least one moisture detector coupled to the at least one processor;
a ball or player detector coupled to the at least one processor;
a motor and drive system coupled to the at least one processor; and
at least one memory coupled to the at least one processor, the at least one memory having computer-executable instructions stored thereon that, when executed by the at least one processor, cause the at least one processor to:
cause the moisture detector to detect a moisture level of grass of a recreational ground;
cause the ball or player detector to detect a ball or player on the recreational ground during game play;
in response to the detection of the ball or player by the ball or player detector, generate a first electronic signal indicative of the ball or player being detected by the recreational grounds monitoring robot; and
communicate the first electronic signal indicative of the ball or player being detected by the recreational grounds monitoring robot to a system controller device.

13. The recreational grounds monitoring robot of claim 12 wherein the ball or player detector comprises a camera and the computer-executable instructions, when executed by the at least one processor, cause the at least one processor to:
cause the camera to capture high speed images of the ball or player while the ball or player is moving;
track a location of the ball or player during game play based on the high speed images of the ball or player captured while the ball or player is moving.

14. The recreational grounds monitoring robot of claim 12 wherein the ball or player detector comprises a laser scanning system and the computer-executable instructions, when executed by the at least one processor, cause the at least one processor to:
cause the laser scanning system to detect a current location of the ball or player on the recreational ground during game play.

15. The recreational grounds monitoring robot of claim 12 wherein the ball or player detector comprises a motion sensor and the computer-executable instructions, when executed by the at least one processor, cause the at least one processor to:
cause the motor and drive system to autonomously move the recreational grounds monitoring robot around the recreational ground as a target for a player to catch or hit with a ball as part of game play or training.

16. The recreational grounds monitoring robot of claim 12 wherein the ball or player detector comprises a camera and the computer-executable instructions, when executed by the at least one processor, cause the at least one processor to:
cause the camera to capture one or more images of an object on the recreational ground during game play; and
perform object recognition identifying the object as being a particular player or the ball during game play; and
during game play on the recreational ground, update one or more of a game score or game statistics based on the object recognition identifying the object as being a particular player or a ball during game play.

17. The recreational grounds monitoring robot of claim 12 wherein the ball or player detector comprises a camera and the computer-executable instructions, when executed by the at least one processor, cause the at least one processor to:
cause the camera to capture one or more images of an object on the recreational ground during game play; and
send the one or more images of the object to the system controller device to perform, during game play, object recognition identifying the object as being a particular player or the ball.

18. The recreational grounds monitoring robot of claim 12 wherein the ball or player detector comprises a camera and the computer-executable instructions, when executed by the at least one processor, cause the at least one processor to:
generate a second electronic signal indicative of the detected moisture level of the grass of the recreational ground; and communicate to a system controller device the second electronic signal indicative of the detected moisture level of the grass of the recreational ground.

19. A non-transitory computer-readable storage medium having computer-executable instructions thereon, that when executed by at least one computer processor, cause the following to be performed:
   cause a recreational grounds monitoring robot to autonomously detect a moisture level of grass of a recreational ground at various different locations on the recreational ground;
   cause the recreational grounds monitoring robot to detect a ball or player on the recreational ground during game play on the recreational ground while the recreational grounds monitoring robot is located outside a playing area on the recreational ground;
   in response to the detection of the ball or player on the recreational ground during game play on the recreational ground, generate a first electronic signal indicative of the ball or player being detected by the recreational grounds monitoring robot; and
   communicate the first electronic signal indicative of the ball or player being detected by the recreational grounds monitoring robot.

20. The non-transitory computer-readable storage medium of claim 19 wherein the computer-executable instructions, when executed by the at least one computer processor, further cause the at least one computer processor to:
   receive at the recreational grounds monitoring robot one or more additional electronic signals indicative of the ball or player being detected by one or more other recreational grounds monitoring robots; and
   determine statistics regarding a path the ball traveled during a game being played on the grass of the recreational ground based on the one or more additional electronic signals indicative of the ball or player being detected by the one or more other recreational grounds monitoring robots.

21. The non-transitory computer-readable storage medium of claim 19 wherein the computer-executable instructions, when executed by the at least one computer processor, cause the at least one computer processor to:
   cause a laser scanning system of the recreational grounds monitoring robot to detect the ball or player on the recreational ground during game play on the recreational ground.

22. The non-transitory computer-readable storage medium of claim 19 wherein the computer-executable instructions, when executed by the at least one computer processor, cause the at least one computer processor to:
   cause a camera of the recreational grounds monitoring robot to move to track motion of the ball or player on the recreational ground during game play; and
   update one or more of: a game score, game statistics and player statistics during game play based on the tracked motion of the ball or player on the recreational ground during game play.

23. The non-transitory computer-readable storage medium of claim 22 wherein the computer-executable instructions, when executed by the at least one computer processor, further cause the at least one computer processor to:
   communicate to one or more of a mobile device and a system controller device information indicating the one or more of: a game score, game statistics and player statistics during game play based on the tracked motion of the ball or player on the recreational ground during game play.

* * * * *